(12) United States Patent
Korhonen

(10) Patent No.: US 6,685,649 B2
(45) Date of Patent: Feb. 3, 2004

(54) MONITORING A CONDITION OF A PATIENT UNDER ANAESTHESIA OR SEDATION

(75) Inventor: Iikka Korhonen, Lempäälä (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/118,855

(22) Filed: Apr. 9, 2002

(65) Prior Publication Data

US 2003/0055343 A1 Mar. 20, 2003

(30) Foreign Application Priority Data

Jul. 4, 2001 (EP) .................................. 01660136

(51) Int. Cl.$^7$ ................................................ A61B 5/02
(52) U.S. Cl. ........................................ 600/485; 600/519
(58) Field of Search ......................... 600/509, 519, 600/521, 485; 607/23, 25

(56) References Cited

U.S. PATENT DOCUMENTS

| | | | | |
|---|---|---|---|---|
| 3,946,725 | A | * 3/1976 | Bolshov et al. | 600/519 |
| 4,788,982 | A | * 12/1988 | Gedeon et al. | 600/483 |
| 5,372,140 | A | * 12/1994 | Pomfrett | 600/513 |
| 5,438,983 | A | 8/1995 | Falcone | |
| 5,871,450 | A | * 2/1999 | Nomura et al. | 600/485 |
| 6,120,443 | A | 9/2000 | Cohen-Laroque | |

FOREIGN PATENT DOCUMENTS

| | | |
|---|---|---|
| EP | 691105 | 1/1996 |
| EP | 774234 | 5/1997 |

OTHER PUBLICATIONS

*A Primer for EEG Signal Processing in Anesthesia*, Ira J. Rampil, Anesthesiology, vol. 89, No. 4, Oct. 1998, pp. 980–1002.

* cited by examiner

Primary Examiner—Mark Bockelman
(74) Attorney, Agent, or Firm—Andrus, Sceales, Starke & Sawall, LLP (57) ABSTRACT

The invention relates to a method for monitoring a condition of a patient under anaesthesia or sedation. In the method a signal (S) is acquired representing a cardiovascular activity of the patient, and periodically repeated waveforms (P) are detected, followed by calculation of time intervals ($T_i$) between, and/or pressures ($B_i$) from, and/or temporal rates ($R_i$) from successive waveforms. Next at least one of the following—a mathematical time series ($T_1$, $T_2$ ... $T_n$, $T_{n+1}$ ...), or a mathematical pressure series ($B_1$, $B_2$ ... $B_n$, $B_{n+1}$ ...), or a mathematical rate series ($R_1$, $R_2$ ... $R_n$, $R_{n+1}$ ...) is/are formed. Further in the method said time series and/or said pressure series and/or said rate series is mathematically filtered to provide successive average values ($\bar{T}_i$; $\bar{B}_i$; $\bar{R}_i$) over a predetermined first time period ($\tau$), and a substantial decrease, or increase respectively in said average values is detected.

42 Claims, 5 Drawing Sheets

Painful stimulus

MONITORING A CONDITION OF A PATIENT UNDER ANAESTHESIA OR SEDATION

FIELD OF THE INVENTION

The present invention relates to a method for monitoring a condition of a patient under anaesthesia or sedation, the method comprising the steps of: acquiring a signal representing temporally a cardiovascular activity of the patient; detecting periodically repeated waveforms in said signal; calculating at least one parameter selected from: time intervals between, or pressures from, or temporal rates from successive waveforms; and forming respectively at least one of the following: a mathematical time series of said time intervals, or a mathematical pressure series of said pressures, or a mathematical rate series of said temporal rates. The invention also relates to a use of the method, in which a signal representing a cardiovascular activity of a patient is analyzed for detection of periodically repeated waveforms, at least one of the following: time intervals between, or pressures from, or temporal rates from successive waveforms are calculated to provide at least one of the following: a mathematical time series of said time intervals, or a mathematical pressure series of said pressures, or a mathematical rate series of said temporal rates, as well as to an apparatus for monitoring a condition of a patient under anaesthesia or sedation, the apparatus comprising: detection means for receiving a substantially continuous electrical signal representing a cardiovascular activity of the patient; a voltage/current dependent circuit detecting each predetermined waveform in said signal; and first calculation means providing at least one of the following: a series of time intervals between successive waveforms, or a series of pressures, or a series of temporal rates from successive waveforms.

RELATED STATE OF THE ART

Concept of the depth of anaesthesia has been of interest for recent decades, and several measures have been proposed to assess the depth of anaesthesia. Recently, however, this unitary anaesthesia theory of the existence of one-dimensional concept called "depth of anaesthesia" has been criticised as oversimplified. Instead it has been suggested that the anaesthesia has not one but three main components: hypnosis, analgesia and muscle relaxation. Different anaesthetic regimens have different effect on these three components. Furthermore, they have effects on both cortical and subcortical levels. An adequate anaesthesia means unresponsiveness to both noxious and non-noxious stimuli. The former may be defined by means of hemodynamic, motor and endocrine stability, while the latter is related to the loss of consciousness and recall and amnesia. In practice the adequate anaesthesia is administered by using a combination of drugs with different effects on brain, spinal cord, autonomic nervous system and neuro-muscular junction. The combination of these effects hence creates the hypnotic, analgesic and muscle relaxing effects.

Heart rate (=HR) is controlled by autonomic nervous system. Especially sympathetic activation to the heart causes heart rate acceleration. Sudden pain causes a stress reaction, which is associated with sympathetic activation leading to sudden increase in HR and blood pressure. Hence, in clinical practise HR and blood pressure responses have been used for decades by experienced anaesthesiologists to heuristically detect inadequacy of anaesthesia. However, not only pain but also various other issues may cause variations in HR and blood pressure, and consequently the HR and blood pressure are continuously varying. Hence, monitoring just the mean level of HR and blood pressure is not sufficient.

Document U.S. Pat. No. 5,372,140 proposes a method and an apparatus for providing a measure of the depth of anaesthesia based on analyzing beat-to-beat heart rate together with respiration. For that purpose a series of so-called R-waves from the cardiac signal is analyzed for determining the position in time of each R-wave relative to the respiratory cycle within which it occurs, and a measurement value representing the degree of clustering is derived. Further a so-called circular statistics is utilized with a test for randomness, and finally the measurement value is compared with a reference value to find the depth of anaesthesia. The proposed measure is related to respiratory sinus arrhythmia, which is primarily controlled by parasympathetic nervous system. The measure is poorly related to the functioning of the sympathetic nervous system, and hence may not measure sympathetic reactions to pain. As a conclusion, the disclosed method and apparatus does not provide results, which could be considered as an objective measure for the level of analgesia of a patient.

Document U.S. Pat. No. 6,120,443 proposes another method and device for determining a depth of anaesthesia by acquiring a plurality of successive signals representing a cardiac activity of the patient, detecting a periodic wave therefrom, calculating time intervals between successive waves, determining a digital series of the time intervals, and calculating a fractal dimension of said series as well as calculating a depth of anaesthesia as a function of the fractal dimension. According to the document the signal is filtered by calculating the maximum correlation between the sampled signal and a theoretical signal, whereupon a signal period between 20 and 80 intervals is suggested, then regrouping the time intervals to form several digital series, and finally the fractal dimension is approximated by determining a dimension of correlation between said digital series, whereupon two to ten series is used. The disclosed method so is mathematically based on computing correlation dimension for beat-to-beat heart rate signal. Theoretically this kind of calculations requires a very long data sequence, leading to large delays in real-time monitoring. Though the inventor proposes to use relatively short data sequences to minimise the acquisition delay this makes the theoretical basis of the method questionable. As above, also this disclosed method and apparatus does not provide results, which could be considered as an objective or reliable measure for the level of analgesia of a patient.

Recently, methods for assessing the hypnotic component especially by monitoring electroencephalographic (EEG) signal have been introduced. The most well-known is the Bispectral Index (BIS), but also fractal spectrum, Lempel-Ziv complexity, Kolgomorov-Sinai entropy and spectral entropy etc. has been studied, e.g. Ira J. Rampil: "A Primer for EEG Signal Processing in Anesthesia"—Anesthesiology, Vol. 87, No. 4, October 1998, and evidently some of them can provide a data describing reliably the level of consciousness independent of the individual. Muscle relaxation may be measured e.g. by monitoring neuro-muscular transmission time and/or excited force, and one method and instrument for this purpose is disclosed in publication EP-0 691 105. Measuring muscle relaxation can be considered to be an established and reliable technology, and it is already a standard practice, because various devices are commercially available, too.

SUMMARY OF THE INVENTION

Accordingly the main object of the invention is to achieve a method and an apparatus for monitoring the anaesthesia or sedation of a patient so that a reliable data about level or depth of analgesia would be available to an anaesthetist or to other purposes. The second object of the invention is to achieve a method and an apparatus for monitoring the anaesthesia or sedation capable of using measured signals derived from various sources of the patient, which means that the method should not be dependent on any single type of detector. The third object of the invention is to achieve a method and an apparatus for monitoring the anaesthesia or sedation capable to deliver such results as an output, with the basis of which the adequacy of analgesia could be reliably enough assessed by inexperienced anaesthetists or other operators, too. The fourth object of the invention is to achieve a method and an apparatus for monitoring the anaesthesia or sedation functioning with an acceptable speed so that a change in analgesia to a hazardous direction is detected and reported early enough to allow timely corrective actions.

The above described problems can be solved and the above defined objects can be achieved by the inventive method, which comprises filtering said time series and/or said pressure series and/or said rate series mathematically to provide a plurality of successive average values each over a predetermined first time period, and detecting a substantial decrease, or increase respectively in said plurality of successive average values; and by the inventive use, in which said time series and/or said pressure series and/or said rate series are mathematically filtered to provide a plurality of successive average values each over a predetermined first time period, and a substantial decrease, or increase respectively in said average values is detected and data of said detection is forwarded to an operator for monitoring adequacy of analgesia of a patient under anaesthesia or sedation; as well as by the inventive apparatus, which comprises second calculation means providing successive average values of the series of said time intervals and/or said pressure series and/or said temporal rates over a predetermined first time period, third calculation means providing data about an decrease, or increase respectively in said successive average values, and a display and/or connections into other devices.

Figure 1:
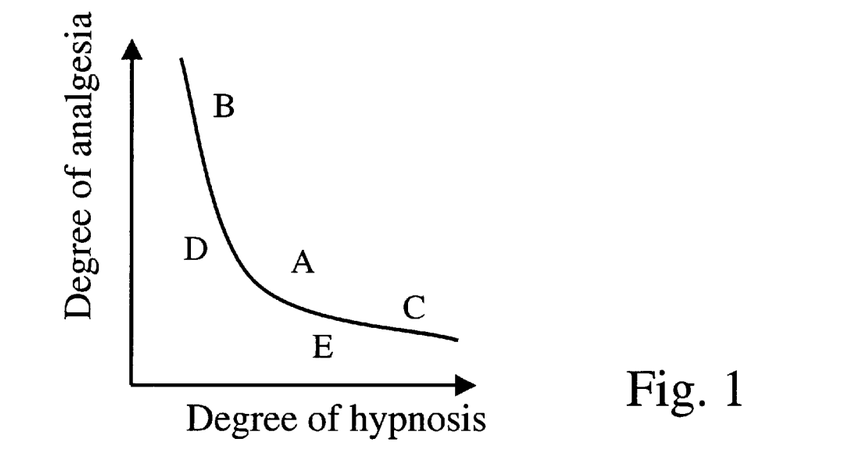
FIG. 1 describes the principle of interdependence between hypnosis and analgesia, whereupon the adequacy of another is dependent of the degree of the other.

The present innovation proposes a method, which enables monitoring a condition of a patient under anaesthesia or sedation, and specifically enables to assess the adequacy of analgesia in anaesthetized or sedated subjects in real time, based on the measurement of sympathetic reactions in beat-to-beat cardiovascular time series or pressure series or heart rate series. In anaesthesia there is a need to assess level of analgesia, i.e. adequacy of pain medication, in order to avoid the subject to feel pain during the operation. This is a complicated task in presence of other medication, such as hypnotic agents and especially muscle relaxants. The invention functions successfully in solving this task and so fills the missing link in the complete anaesthesia monitoring. Especially for analgesia and hypnosis, the adequacy of another is dependent on the level of the other one as schematically shown in FIG. 1. In area D the degree or level of analgesia is acceptable as such, but the degree or level of hypnosis is quite too low, which case corresponds a local analgesia or anaesthesia and is not practical in many cases. In area E the degree of hypnosis is acceptable as such, but the degree of analgesia is quite too low, whereupon the patient does not have consciousness during operation and does not remember anything about the operation afterwards, but the pain of the operation cause traumatic symptoms anyway. In area B the degree of analgesia is high enough so that a lower degree of hypnosis can be utilized, and in area C the degree of hypnosis is high enough so that a lower degree of analgesia can be utilized. In area A both the analgesia and the hypnosis has optimal levels, but generally points on the right hand side of the curve in FIG. 1 are useful and points on the left hand side of the curve shall be avoided during total anaesthesia. For optimal total anaesthesia all the three components, that are analgesia, hypnosis and muscle relaxation should be controlled. This requires methods to independently assess all the components. This innovation is based on the facts that pain causes a sympathetic activation. Sympathetic activation propagates via sympathetic nervous branches to different sites of the body, including heart and blood vessels. In blood vessels the activation causes vasoconstriction and increases hence blood pressure. In the heart sympathetic activation causes heart rate acceleration.

Actual heart rate is defined by the net effect of sympathetic and parasympathetic activity to the heart. An acceleration of heart rate may be caused either by sympathetic activation or withdrawal of parasympathetic activity, or both. A deceleration is caused if opposite changes in activity occurs. The amplitude or levels of the systemic arterial blood pressure behave in an analogous way. A sudden increase of blood pressure is caused by the sympathetic activation, while a decrease is primarily caused by the decrease in the sympathetic activation—in case sudden changes in fluid balance can be excluded. Due to continuous modulation in both sympathetic and parasympathetic activity the beat-to-beat heart rate is continuously varied, which is called heart rate variability (HRV). The presence of HRV complicates the identification of e.g. heart rate accelerations due to sympathetic activation. However, the time constants of the parasympathetic and sympathetic responses are different. For the former the response time is a few hundreds of milliseconds while for the latter the response starts only after a couple of seconds. Hence, it is possible to filter out short-term HRV primarily caused by parasympathetic activity, and hence emphasise the sympathetic activity in the signal. Furthermore, by picking up heart rate accelerations it is further possible to emphasise features, which are most potentially related to sympathetic activation. It should be noted that sympathetic reactions might be caused by other reasons than pain, such as physical exercise, mental stress, drugs, etc., too However, in anaesthetized or sedated subjects these other or external stimuli and factors, in addition to potential pain caused by surgery or care actions, are few and may be largely controlled by the care team. Though the reaction itself is not specific for pain and analgesia, it is possible to discriminate whether the identified reaction was due to pain or not by using this other information available for the care team. Hence, excluding the short-term effects of various drugs, the sympathetic reactions are potential markers for pain, and so concerning anaesthetized and sedated subjects, heart rate accelerations are potential markers for inadequate analgesia. The present innovation proposes a method to quantify the inadequate analgesia through one of the heart rate acceleration indexes and/or a blood pressure index, with the respective intermediates, too.

The present innovation comprises a step of acquiring at least one signal representing the subject's cardiac activity, a step of detecting the position of a waveform representing each single heart beat in the signal, a step of constructing a beat-to-beat signal by calculating the time difference or temporal rates like frequency of these waveforms, or alternatively a step of calculating the blood pressures of these waveforms, a step for filtering this signal to suppress non-sympathetic variations, a step for detecting potentially sympathetic reactions in the filtered signal, and a step for calculating a statistic related to the said potentially sympathetic reactions.

Figure 2A:
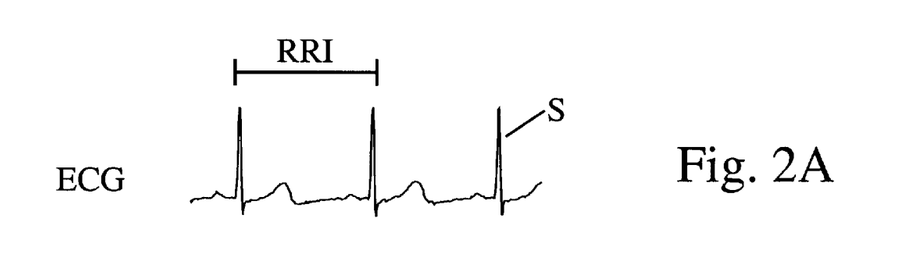
FIGS. 2A–2C are schematic illustrations of the typical signals used for the invention and their functional components for detecting waveforms and for determining time intervals or temporal rates of the heart function, in this case from ECG, or determining pressures of the heart functioning, in this case from blood pressure.
Figure 2B:
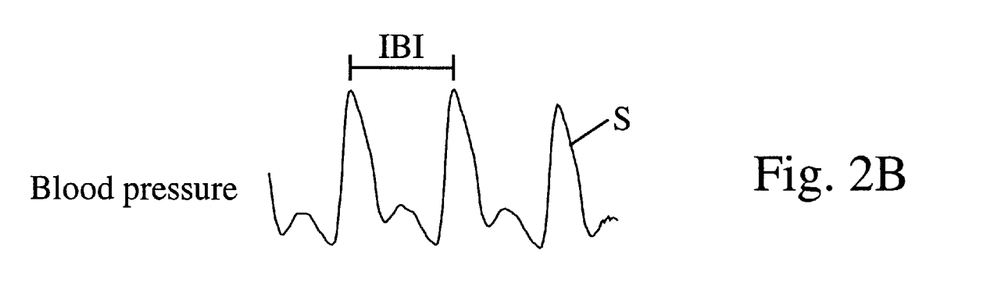
Figure 2C:
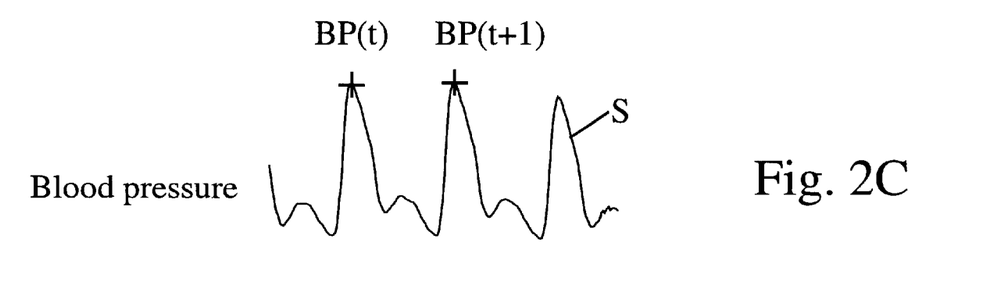

The signal S can be derived preferably from ECG but also from blood pressure, from blood flow velocity, from a light or other electromagnetic radiation absorption factor of blood, from oxygen content of the blood, from acoustic signal emitted by heart or from any other known or new signal or from any combination of the these signals or other known or new signals, which is dependent on cardiovascular activity of the patient and allows to determine a beat-to-beat property of the heart. As examples FIG. 2A shows a signal S received from ECG generally, and FIGS. 2B and 2C show signals S received from blood pressure generally, and the other signals received from other kind of detections typically resemble these shown signals. In general, any signal, which would allow measuring sympathetic reactions, would do. Because the methods and apparatuses to acquire this kind of signals are generally known this step is not described more in detail.

Detecting the waveform P means finding a specific repeating point in the continuously variable signal acquired corresponding reliably and precisely enough to the beat-to-beat phenomenon or the pressure phenomenon of the heart so that the variable time between successive and similar or respective points of the signal, or the pressure difference between or the level in successive points of the signal can be established. A periodically repeated waveform P in the signal is so to be detected. There exist multitude of known and published methods to do this, and accordingly these methods are not described in detail. These methods include e.g. detection of a specific waveform present in the measured signal and representing a single heartbeat, such as R-wave in ECG, systolic pressure in blood pressure curve, maximum derivative in blood flow or blood pressure signal, etc. Furthermore, the methods include computing cross-correlation function of the signal and defining the inter-beat interval from the successive local maximums of the cross-correlation signal, and using a matched filter for the same purpose, etc. Preferably R-to-R interval (RRI) signal, generally the time interval $T_i$, which is calculated as a time difference between the successive R-waves, or a heart rate (HR), generally the temporal rate $R_i$, which is calculated as a frequency between the successive R-waves, is used, as shown in FIG. 2A. Respective time intervals $T_i$ or temporal rates $R_i$ can be determined on the basis of inter-beat-interval (IBI) defined from systolic pressure time instants in blood pressure signal, as shown in FIG. 2B, or the pressures $B_i$ of the pulses on the basis of systolic blood pressure (BP) values in blood pressure signal, as shown in FIG. 2C, or any other known or new waveform. These calculated successive time intervals $T_i$ form a mathematical time series $T_1, T_2 \ldots T_{n-1}$, $T_n, T_{n+1} \ldots$, and respectively these calculated successive temporal rates $R_i$ form a mathematical rate series $R_1$, $R_2 \ldots R_{n-1}, R_n, R_{n+1} \ldots$, or these calculated successive pressures form a mathematical pressure series $B_1, B_2 \ldots B_{n-1}, B_n, B_{n+1} \ldots$.

The time series and rate series respectively is then mathematically filtered to suppress signal components in the series caused by non-sympathetic activity, and hence to emphasize data corresponding sympathetic activity. In this step e.g. a plurality of successive average values $\overline{T}_i, \overline{B}_i, \overline{R}_i$ are formed from said time series or said rate series. Potentially sympathetic reactions in the filtered data signal can be detected as the shortening of e.g. the R-to-R-interval, or alternatively as the rise or increase of the HR-number, or as the increase of the blood pressure, i.e. the systolic pulses BP or any other levels or amplitudes, which processed data signal can be called a trend signal, which means signal components having a predetermined trend caused by sympathetic activity and so not suppressed. Preferably, only those parts related to potentially sympathetic reactions are restored, the other parts of the samples or time/rate series are suppressed e.g. by assigning them to zero. It shall be understood that there are several mathematical methods to suppress those samples not related to potentially sympathetic reactions and so to produce a trend signal describing sympathetic activity.

The statistic emphasising the potentially sympathetic reactions is calculated after above mentioned detection step. Preferably this is achieved by e.g. calculating a windowed sliding sum of the trend signal, which was formed in the previous step. Alternatively or in addition, a threshold may be used and only trend signals greater than the predetermined threshold are included. The statistic may also be normalised for example by setting the reference value to some well-defined period during the monitoring, or to some reference value obtained from larger studies.

The data concerning the detected decrease, or increase respectively of said average values, that is the emphasized data, is finally forwarded to an anaesthetist or other operator for monitoring adequacy of analgesia of a patient under anaesthesia or sedation. Further and according to requirements of operation also data describing muscle relaxation of said patient and/or data describing the loss of consciousness, together with the above described data of detection concerning analgesia, are forwarded to the operator. It is also possible to measure and receive signals S to provide two or all three of the variables discussed, that is time intervals and/or heart rates and/or pressures of cardiovascular activity and perform the respective calculations, and finally report the results or some of the intermediate results with or without their comparison to the anaesthetist/operator or to some other use. Most probable, if necessary, is the measuring of pressures $B_i$ and in addition either time intervals $T_i$ or temporal rates $R_i$ with respective further calculations, because the meanings of two latter time variables are in fact identical, while the meaning of pressure variables may be deviating. In any case at least one of these three signals is acquired and the respective variables $T_i$, or $B_i$, or $R_i$ is calculated with further calculations and analysis.

The apparatus according to the invention is provided with proper detector(s) for receiving a substantially continuous electrical signal S representing a cardiovascular activity of the patient, electrical circuits capable of detecting the predetermined points P in the signal, and proper calculation means, e.g. micro-processors, capable of performing the necessary calculations, as well as a display and/or connections for reporting those results and/or intermediate results of calculations needed. Useful components for the apparatus are commercially available, and so they are not described in detail.

BRIEF DESCRIPTION OF THE DRAWINGS

The invention and its preferred embodiments are now described more in detail with reference made to the accompanying drawings.

DETAILED DESCRIPTION OF THE PREFERRED EMBODIMENTS

Figure 4A:
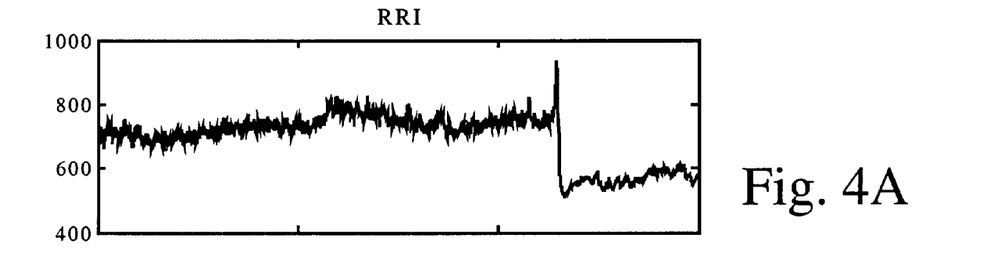
FIG. 4A is an example illustrating the time series of R-to-R Intervals (=RRI) sampled form an ECG signal during sevoflurane anaesthesia and adenoidectomy in an 8-year-old child.
Figure 5A:
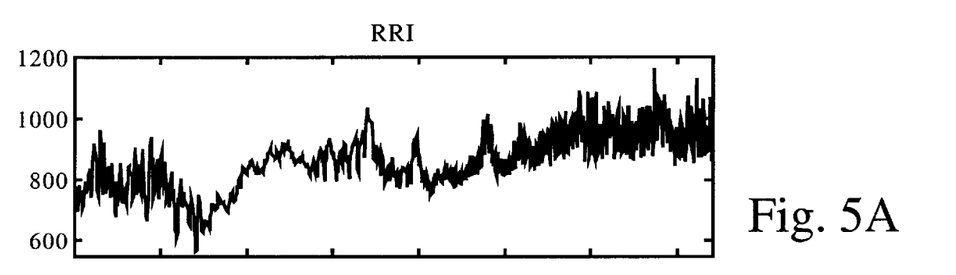
FIGS. 5A–5B are an example illustrating RRI signal and derived $HRA_{index}$ signal during a short surgery. Painful surgical stimulus causes movement responses, which are accompanied or even preceded by an increase in the $HRA_{index}$. Induction to anaesthesia causes the $HRA_{index}$ to fall and awakening it to rise.
Figure 6:
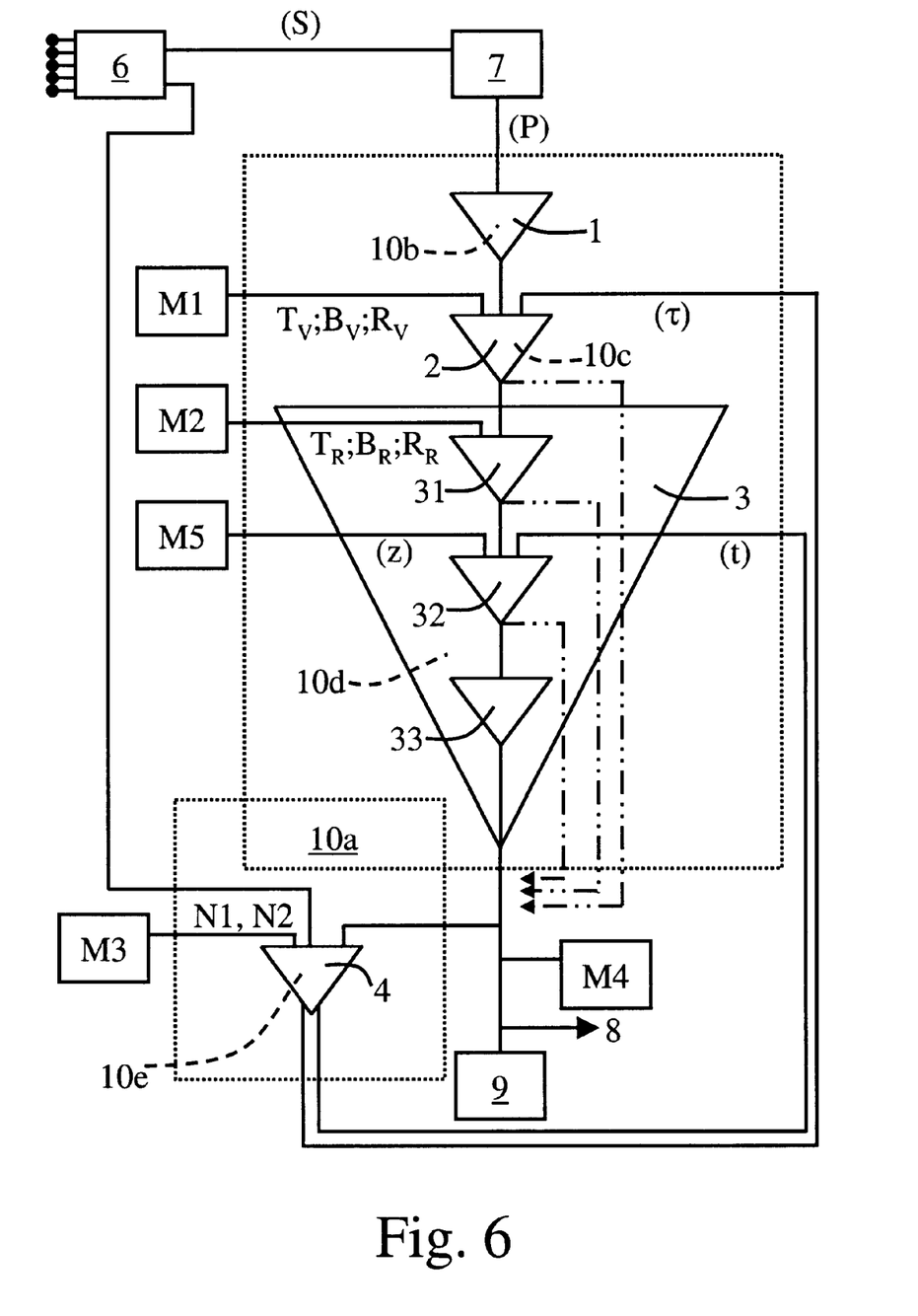
FIG. 6 shows schematically the typical blocks of an apparatus according to the invention, the apparatus being capable of performing calculations for the intermediate results and final results illustrated in FIGS. 4A to 4D and 5A to 4B, and according to the steps of the invention.

As already mentioned the method for monitoring a condition of a patient under anaesthesia or sedation comprises at first the step of acquiring a signal S representing temporally a cardiovascular activity of the patient. This acquiring can be performed using any method and any detection means 6 capable of receiving a substantially continuous electrical signal S corresponding the cardiac pulses of the patient in a useful form. The signal S is received by measuring electrical manifestations of cardiac actions like electrocardiography, or a flow velocity of blood, or pressure of blood, or an absorption of electromagnetic radiation by blood, or acoustical manifestations emitted from bloodvascular system. The periodically repeated waveforms P, which are typically a predetermined type or section in a signal curve, for instance a specific point—R-wave, or any respective change in signal level, or any respective point providing a change in direction of the signal curve, e.g. a signal peak etc.—in said signal level is then detected by a voltage and/or current dependent circuit 7 of the apparatus. Next either time intervals $T_i$ between successive waveforms, or alternatively pressures $B_i$ from successive waveforms, or alternatively temporal rates $R_i$ from successive waveforms are calculated. The temporal rate R is actually a frequency and so an inverse value of time intervals T. The pressures $B_i$ are dependent on the signal strength values. After at least two intervals/rates-calculation a mathematical time series $T_1, T_2 \ldots T_n, T_{n+1} \ldots$ of said time intervals, or a mathematical pressure series $B_1, B_2 \ldots B_n, B_{n+1} \ldots$ of said pressures, or a mathematical rate series $R_1, R_2 \ldots R_n$, $R_{n+1} \ldots$ of said temporal rates are formed. The time span for calculating the temporal rates can be equal with the first time period discussed later, or any other time period. These calculations of time intervals $T_i$ or pressures $B_i$ or temporal rates $R_i$ and arrangement into said series are performed by the first calculation means 1 of the apparatus. FIGS. 4A and 5A illustrates graphically time series $T_1, T_2 \ldots T_n$, $T_{n+1} \ldots$ in two different cases, in which the signals S are acquired from the RRI of an ECG. In this context it shall be mentioned that the pressure series of the blood pressure may be formed by using various different fiducial points in the blood pressure waveform, such as the systolic or diastolic pressure, their difference that is amplitude or pressure difference, any mean pressure or some other derivation of the successive pulses. The change from waveform BP(n) to the next waveform BP(n+1) is effectively the basis to the further calculations just like with calculations utilizing temporal rates and time intervals. In this text the definition 'pressure' means the values in any of the applicable fiducial points or any applicable pressure difference.

Figure 4B:
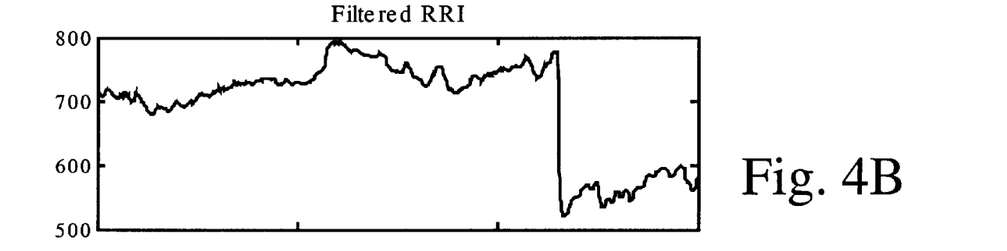
FIG. 4B illustrates the RRI data signal of FIG. 4A filtered according to one embodiment of the invention, the filter being a median filter with length of 40 heart beats.
Figure 5B:
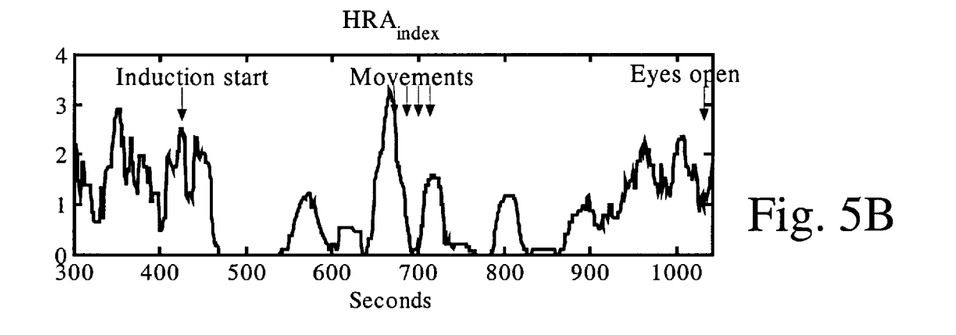

The method further comprises the step of filtering said time series or said rate series mathematically to provide a plurality of successive average values $\overline{T}_i$ or $\overline{B}_i$ or $\overline{R}_i$ each over a predetermined first time period $\tau$, which calculation step is performed by second calculation means 2 of the apparatus. In this context, the definition average value means any type non-weighted or weighted value formed from a group of values and representing generally the whole group. Arithmetic mean values and median values are the most often used, generally known, and also practical for the purposes of the invention, but also geometric means or harmonic means etc. can be useful. The average values $\overline{T}_i$ or $\overline{B}_i$ or $\overline{R}_i$ are preferably sliding even medians or arithmetic mean values of the time intervals $T_i$ or pressures $B_i$ or temporal rates $R_i$, or sliding weighted medians or arithmetic mean values of the time intervals $T_i$ or pressures $B_i$ or temporal rates $R_i$ respectively calculated over said first time period $\tau$. This predetermined first filter length or first time period $\tau$ for the filtering is typically between 20 and 60 beats of heart to suppress non-sympathetic activity and hence emphasise sympathetic activity. For attaining the first time period $\tau$, which is dependent on the heart rate HR, the apparatus further comprises fourth calculation means 4 connected to the detection means 6 to receive the signal S and at least to the second calculation means 2, whereupon the fourth calculation means 4 preferably feeds a first predetermined number N1 of heart beats as the first time period $\tau$ into said second calculation means 2. It is also possible to utilize a constant first time period $\tau$. The fourth calculation means 4 is connected to a third memory means M3, which is storing at least the predetermined number N1 or the time period $\tau$. For the examples as illustrated in FIGS. 4B and 5B a median filter with length $\tau$ was used. Other filters such as finite impulse response filters with suitable characteristics might be used, too. The filtering using the first time period $\tau$ as disclosed above is a preferred embodiment, but alternatively the filtering can be performed also, or in combination with the preferred alternative, by comparing the time intervals $T_i$ or pressures $B_i$ or temporal rates $R_i$ with a predetermined threshold value $T_v$; $B_v$; $R_v$ with inclusion only values detected to be smaller, or greater respectively than said threshold value, whereafter the plurality of successive average values $\overline{T}_i$; $\overline{B}_i$; $\overline{R}_i$ is calculated. If necessary giving an alarm is possible in case the time intervals $T_i$ or pressures $B_i$ or temporal rates $R_i$ are found to bee too low or high as compared to the threshold values. The apparatus further comprises a first memory means M1 connected to the second for storing at least the above mentioned predetermined values $T_v$; $B_v$; $R_v$.

An essential step in the method of invention is the detection of a substantial decrease, in case of time intervals $T_i$, or an increase, in case of temporal rate $R_i$ or in case of pressure $B_i$ of the plurality of successive average values $\overline{T}_i$; $\overline{B}_i$; $\overline{R}_i$, which is performed, generally speaking, by the third calculation means 3 of the apparatus. For this general step the average values $\overline{T}_i$ or $\overline{B}_i$ or $\overline{R}_i$ are firstly mathematically derived, whereupon temporally variable derivatives $d\overline{T}_i$ or $d\overline{B}_i$ or $d\overline{R}_i$ are received as intermediate results of the calculations. Derivations are processed e.g. by the first calculation unit 31 of the third calculation means 3, or in some other processor as is described later. These derivatives $d\overline{T}_i$; $d\overline{B}_i$; $d\overline{R}_i$ are a basic data about the decrease, or increase respectively of the successive average values. It is possible to feed the derivatives to a display 9 and/or connections 8 into other devices, but it is advantageous to continue calculation in order to have more clear data for evaluation.

Figure 4C:
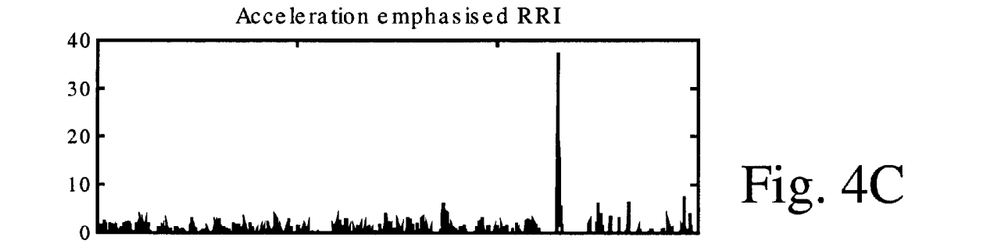
FIG. 4C illustrates the data signal of FIG. 4B emphasized according to one embodiment of the invention, the filtered data signal being mathematically derived describing the acceleration of the change in RRI.

In the general step of decrease/increase detecting those values of said derivatives which are decreasing $d\overline{T}_i<0$, or increasing $d\overline{R}_i>0$ and $d\overline{B}_i>0$ respectively are secondly emphasized as follows. The emphasizing is performed by neglecting and/or suppressing those values of said derivatives, which are not decreasing/increasing at all, and/or not decreasing/increasing enough. Said neglecting and/or suppressing preferably comprises applying a mathematical operator Z into said temporally variable derivatives $d\overline{T}_i$ or $d\overline{B}_i$ or $d\overline{R}_i$ to have a selection of accelerations $T_a(t)$ or $B_a(t)$ or $R_a(t)$ describing the decrease of time interval derivatives $d\overline{T}_i$, or increase of temporal rate derivatives $d\overline{R}_i$ or increase of pressure derivatives $d\overline{B}_i$ each describing the increase of the cardiovascular activity only. Actually any predetermined mathematical operation capable of selecting more valid, that means a higher value with correct sign, derivatives $d\overline{T}_i$ or $d\overline{B}_i$ or $d\overline{R}_i$ from less valid derivatives can be useful. The third calculation means 3 of the apparatus can comprise a second calculation unit 32 applying this above mentioned mathematical operator Z to said derivatives, and a fifth memory means M5 for storing at least the mathematical operators Z if necessary. Accordingly the selection of accelerations $T_a(t)$ or $B_a(t)$ or $R_a(t)$ includes only those of said temporally variable derivatives $d\overline{T}_i$ or $d\overline{B}_i$ or $d\overline{R}_i$ respectively, which are of a type or types predetermined as relevant and/or fulfil criteria of said type(s) under a second time period t. So a plurality of accelerations $T_a(t)$ to be further processed mathematically is a subset of the total set of variable derivatives $d\overline{T}_i$, and in a respective way a plurality of accelerations $R_a(t)$ to be further processed mathematically is a subset of the total set of variable derivatives $d\overline{R}_i$, and in a respective way a plurality of accelerations $B_a(t)$ to be further processed mathematically is a subset of the total set of variable derivatives $d\overline{B}_i$. These selections of accelerations $T_a(t)$ or $B_a(t)$ or $R_a(t)$ may in some cases, e.g. for an experienced anaesthetist, be useful as such, as can be seen from FIG. 4C. As an additional feature the respective one of the temporally variable derivatives $d\overline{T}_i$; $d\overline{B}_i$; $d\overline{R}_i$ and/or the respective one of the selections of accelerations $T_a(t)$; $B_a(t)$; $R_a(t)$ concerning time intervals or temporal rates can be compared with one or several predetermined reference values $T_R$; $B_R$; $R_R$, whereupon only those values of the derivatives or accelerations being below, or exceeding respectively said reference value(s) are reported or forwarded to further calculations. In the apparatus the third calculation means 3 or the second calculation unit 32 thereof is connected to a second memory means M2 for storing at least the predetermined values $T_R$; $B_R$; $R_R$.

Figure 3:
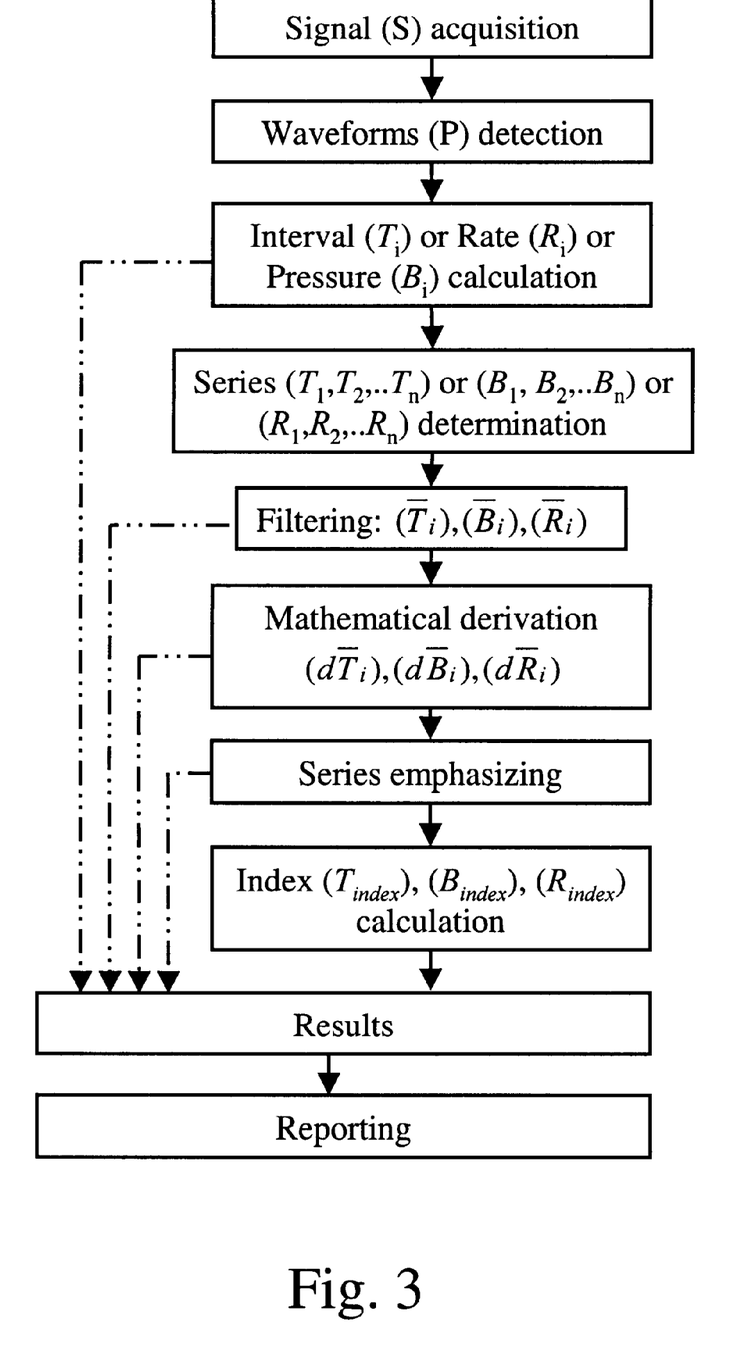
FIG. 3 shows the main steps of processing or calculating the signal from measured ECG or blood pressure signals, as an example.
Figure 4D:
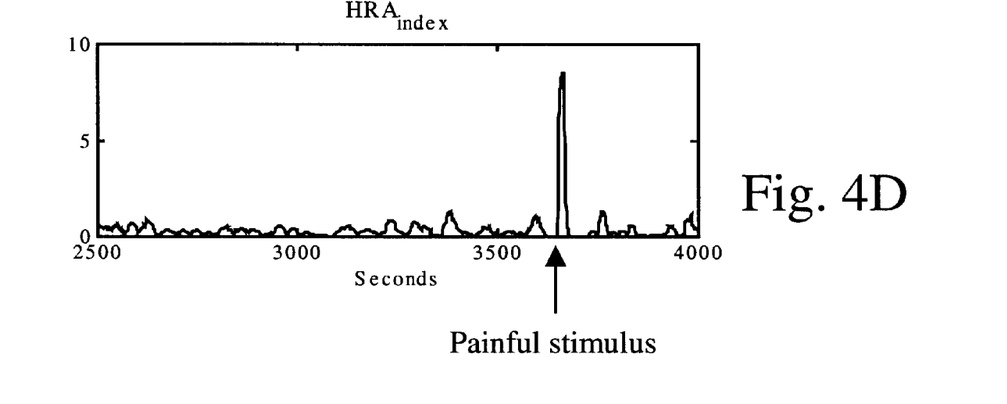
FIG. 4D illustrates the data signal of FIG. 4C after performing selection according to one embodiment of the invention, a windowed sliding summing of a length of 60 heart beats and further a mathematical sign operator being applied to the acceleration data, whereupon a $HRA_{index}$ signal as the final result, which is forwarded to a display or to another device.

Within this general step of decrease/increase detecting said emphasizing is thirdly performed over a predetermined second time period t using one or more of the following alternatives. According to one preferred alternative a sliding sum of said selected accelerations $T_a(t)$ or $B_a(t)$ or $R_a(t)$ over said second time period t is calculated, whereupon the respective one of the selections of accelerations $T_a(t)$; $B_a(t)$; $R_a(t)$ is in this way evaluated, which evaluation offers an acceleration index $T_{index}$ or $B_{index}$ or $R_{index}$ respectively as a final result. FIGS. 4D and 5B illustrates the acceleration index $R_{index}$, in practice $HRA_{index}$, and it can be seen that both for the simple case —FIG. 4D—and for the more complicated case—FIG. 5B—acceleration index provides very clear and concise result, which is easy to understand. For this evaluation the predetermined second time period t is preferably between 20 and 120 beats of heart. According to another alternative the selection of accelerations $T_a(t)$ or $B_a(t)$ or $R_a(t)$ are compared with one or several predetermined reference values $T_R$ or $B_R$ or $R_R$ respectively, and only those values of the accelerations being below, or respectively exceeding said reference value(s) are reported as an acceleration index $T_{index}$; $B_{index}$; $R_{index}$. This last mentioned comparison can be utilized e.g. for an alarm, too. In the apparatus of the invention the third calculation means 3 comprises a third calculation unit 33 for applying the mathematical sliding sum of said selection of accelerations, or for comparing the acceleration with the reference values $T_R$ or $B_R$ or $R_R$. Anyway at least the respective one of the acceleration indexes $T_{index}$; $B_{index}$; $R_{index}$ is reported. It is of course possible to report whichever intermediate results of calculations as shown in FIG. 3. For attaining the second time period t, which is dependent on the heart rate HR, the apparatus can utilize the fourth calculation means 4 disclosed earlier in this text, the fourth calculation means 4 being connected to the detection means 6 to receive the signal S and at least to the second calculation unit 32 of the third calculation means 3, whereupon the fourth calculation means 4 preferably feeds a second predetermined number N2 of heart beats as the second time period t into said second calculation unit 32. It is also possible to utilize a constant second time period t. The third memory means M3 connected to the fourth calculation means 4 stores the predetermined number N2 or the time period t according to what is needed.

In the use of the inventive method, a substantial decrease, or increase respectively in said average values $\overline{T}_i$; $\overline{B}_i$; $\overline{R}_i$, and/or the temporally variable derivatives $d\overline{T}_i$; $d\overline{B}_i$; $d\overline{R}_i$, and/or more preferably the selection of accelerations $T_a(t)$; $B_a(t)$; $R_a(t)$, and/or at least the acceleration index $T_{index}$; $B_{index}$; $R_{index}$, are mathematically detected and data of said detection is forwarded to an operator for monitoring adequacy of analgesia of a patient under anaesthesia or sedation. Any of the above mentioned intermediate results as well as the final result—acceleration index or variable derivative —describes the change in cardiovascular activity and so serve as the detection of the decrease/increase in the plurality of successive average values, but the further the inventive calculations are proceeded the clearer and more discernible any noticeable change is. Data describing muscle relaxation of said patient received from another system or part of the system, not disclosed in this text but exemplified e.g. in publication EP-0 691 105, and/or data describing the loss of consciousness from another system or part of the system, not disclosed in this text but exemplified e.g. in publication WO-01/24691, together with said data of detection concerning analgesia according to system, that is method or apparatus of the invention, are forwarded to the operator. Said data of detection concerning analgesia is forwarded to the operator preferably in the form of an acceleration index $T_{index}$ or $B_{index}$ or $R_{index}$ being larger than zero, which are the most clear and useful form. It is possible to forward also one or more of the intermediate results to the operator, e.g. temporally variable derivatives $d\overline{T}_i$ or $d\overline{B}_i$ or $d\overline{R}_i$ decreasing $d\overline{T}_i<0$ of said time intervals $T_i$, or increasing $d\overline{R}_i>0$ of said temporal rates, or increasing $d\overline{B}_i>0$ of said pressures $B_i$ respectively, or a selection of accelerations $T_a(t)$ or $B_a(t)$ or $R_a(t)$.

Next an example is disclosed describing calculation of $HRA_{index}$ statistic in practice. First, the electrocardiography (ECG) is monitored, and R-waves of the ECG QRS-complex are being detected. Beat-to-beat $RRI_i$(R-to-R Interval) signal is formed as a time difference of successive R-waves. Then, a median filter of length $\tau$ is applied on this signal to compute a data signal, which emphasises different HR levels in the $RRI_i$, data signal, whereupon a data signal of $\overline{RRI}_i$. A derivative of this signal, $d\overline{RRI}_i$, indicates changes in the HR level. A sign operator Z is then applied to pick up only HR accelerations:

$$RRI_a(t)=0.5\times d\overline{RRI}_i(t)\times\{Z\times[d\overline{RRI}_i(t)]-1\}, \quad (I)$$

whereupon the sign operator Z means the following truth table:

| $d\overline{RRI}_i(t)$ | $Z =$ | (II) |
|---|---|---|
| $> 0$ | 1 | |
| $= 0$ | 0 | |
| $< 0$ | $-1$ | |

$HRA_{index}$ (=HR acceleration index) is then defined as a t-point running average of $RRI_a(t)$. The first length $\tau$ of the first mathematical filter or the second calculation means 2 is used to provide a proper type of data for emphasizing HR accelerations due to increase in the sympathetic activity. The second length t of the second mathematical filter or the third calculation means 3 is used to smooth the output signal $HRA_{index}$ to be convenient for the use. The $HRA_{index}$ effectively show any sympathetic reactions on HR during anaesthesia. Frequent and/or large reactions especially associated with potentially painful stimuli may be considered as a sign of insufficient analgesia.

In the apparatus according to the invention the first calculation means 1, the second calculation means 2 and the third calculation means 3 are preferably a single programmed processor 10a, but can alternatively be comprised of a combination of several programmed processors 10b, 10c, 10d, . . . . For example at least the first calculation means and/or the second calculation means and/or the third calculation means are/is a separate programmed processor. The fourth calculation means 4 can either be included in said single programmed processor 10a, or included in the combination of several programmed processors 10b–10d, or the fourth calculation means can be a separate programmed processor 10e. In practice the one or several programmed processors 10a–10e with the memories M1–M5 are a computer. Components and parts as well as programs for such a computer are commercially available, and so the apparatus is not described more in detail.

What is claimed is:

1. A method for monitoring a condition of a patient under anaesthesia or sedation, the method comprising the steps of:

acquiring a signal representing temporally a cardiovascular activity of the patient;

detecting periodically repeated waveforms in said signal;

calculating at least one parameter selected from:
time intervals between said successive waveforms, pressures from said successive waveforms, temporal rates from said successive waveforms;

forming respectively at least one of the following:
a mathematical time series of said time intervals, or a mathematical pressure series of said pressures, or a mathematical rate series of said temporal rates;

filtering said time series and/or said pressure series and/or said rate series mathematically to provide a plurality of successive average values each over a predetermined first time period; and detecting a substantial decrease, or increase respectively in said plurality of successive average values.

2. A method of claim 1, wherein said step of decrease/increase detecting comprises:

Firstly, a mathematical derivation of said plurality of successive average values to have temporally variable derivatives thereof.

3. A method of claim 2, wherein said step of decrease/increase detecting further comprises:

Secondly, emphasizing those values of said derivatives of said plurality of successive average values of said time series decreasing, whereupon said emphasizing is performed by neglecting and/or suppressing those values of said derivatives which are not decreasing.

4. A method of claim 3, wherein said neglecting and/or suppressing comprises applying a mathematical operator into said temporally variable derivative to have a selection of decreasing accelerations describing the increase of the cardiovascular activity only.

5. A method of claim 4, wherein said selection of accelerations are compared with one or several predetermined reference values, and only values of the accelerations being below said reference value(s) are reported or forwarded to further calculations.

6. A method of claim 3, wherein said step of decrease/increase detecting further comprises:

Thirdly, performing said emphasizing over a predetermined second time period.

7. A method of claim 6, wherein said emphasizing is performed by evaluating said selection of accelerations utilizing a sliding sum of said selected accelerations over said second time period, whereupon said selection provides an acceleration index as a result.

8. A method of claim 7, wherein at least one of said acceleration indexes is reported.

9. A method of claim 6, wherein said predetermined second time period is between 20 and 120 beats of heart.

10. A method of claim 2, wherein said step of decrease/increase detecting further comprises:

Secondly, emphasizing those values of said derivatives of said plurality of successive average values of said pressure series and/or said rate series increasing, whereupon said emphasizing is performed by neglecting and/or suppressing those values of said derivatives which are not increasing.

11. A method of claim 10, wherein said neglecting and/or suppressing comprises applying a mathematical operator into said temporally variable derivative to have a selection of increasing accelerations describing the increase of the cardiovascular activity only.

12. A method of claim 11, wherein said selection of accelerations are compared with one or several predetermined reference values, and only values of the accelerations exceeding said reference value(s) are reported or forwarded to further calculations.

13. A method of claim 10, wherein said step of decrease/increase detecting further comprises:
   Thirdly, performing said emphasizing over a predetermined second time period.

14. A method of claim 13, wherein said emphasizing is performed by evaluating said selection of accelerations utilizing a sliding sum of said selected accelerations over said second time period, whereupon said selection provides an acceleration index as a result.

15. A method of claim 14, wherein at least one of said acceleration indexes is reported.

16. A method of claim 13, wherein said predetermined second time period is between 20 and 120 beats of heart.

17. A method of claim 2, wherein said temporally variable derivatives are compared with one or several predetermined reference values, and only values of the derivatives being below, or exceeding respectively said reference value(s) are reported or forwarded to further calculations.

18. A method of claim 1, wherein said average value is a sliding even median or a sliding mean value of said time intervals or said pressures or said temporal rates, or a sliding weighted median or a sliding weighted mean value of said time intervals or said pressures or said temporal rates respectively calculated over said first time period.

19. A method of claim 1, wherein said decrease/increase in the plurality of successive average values is compared with a predetermined threshold change value, whereupon only values of said time series smaller than said threshold value is forwarded for further calculations and/or for reporting and/or for an alarm is given in case said average values are smaller than said threshold value.

20. A method of claim 1, wherein said decrease/increase in the plurality of successive average values is compared with a predetermined threshold change value, whereupon only values of said pressure series and/or said rate series greater than said threshold value is forwarded for further calculations and/or for reporting and/or for an alarm is given in case said average values are greater than said threshold value.

21. A method of claim 1, wherein said predetermined first time period for said filtering is between 20 and 60 beats of heart.

22. A method of claim 1, wherein said step of acquiring signal is performed by measuring electrical manifestations of one of the following:
   cardiac actions, or a flow velocity or pressure of blood, or an absorption of electromagnetic radiation by blood, or acoustical manifestations emitted from blood-vascular system.

23. A method in which:
   a signal representing a cardiovascular activity of a patient is analyzed for detection of periodically repeated waveforms,
   at least one of the following:
   time intervals between successive waveforms, or pressures from successive waveforms, or temporal rates from successive waveforms are calculated to provide at least one of the following:
      a mathematical time series of said time intervals, or a mathematical pressure series of said pressures, or a mathematical rate series of said temporal rates,
   said time series and/or pressure series and/or said rate series are mathematically filtered to provide a plurality of successive average values each over a predetermined first time period,
   a substantial decrease, or increase respectively in said average values is detected, and
   data of said detection is forwarded to an operator for monitoring adequacy of analgesia of a patient under anaesthesia or sedation.

24. A method of claim 23, wherein said data of detection concerning analgesia is forwarded to the operator in form of temporally variable derivatives of:
   said time intervals, decreasing; or
   said temporal rates, or said pressures respectively, increasing.

25. A method of claim 23, wherein said data of detection concerning analgesia is forwarded to the operator in form of temporally variable derivatives of acceleration index received from a selection of accelerations by a predetermined mathematical operation.

26. A method in which:
   a signal representing a cardiovascular activity of a patient is analyzed for detection of periodically repeated waveforms,
   at least one of the following:
   time intervals between successive waveforms, or pressures from successive waveforms, or temporal rates from successive waveforms are calculated to provide at least one of the following:
      a mathematical time series of said time intervals, or a mathematical pressure series of said pressures, or a mathematical rate series of said temporal rates,
   said time series and/or pressure series and/or said rate series are mathematically filtered to provide a plurality of successive average values,
   a decrease, or an increase respectively in said average values is detected, and
   data of said detection is forwarded to an operator for monitoring adequacy of analgesia of a patient under anaesthesia or sedation, together with data describing muscle relaxation of said patient and/or data describing loss of consciousness obtained by other means.

27. A method of claim 26, wherein said data of detection concerning analgesia is forwarded to the operator in form of temporally variable derivatives of:
   said time intervals, decreasing; or
   said temporal rates, or said pressures respectively, increasing.

28. A method of claim 26, wherein said data of detection concerning analgesia is forwarded to the operator in form of temporally variable derivatives of acceleration index received from a selection of accelerations by a predetermined mathematical operation.

29. An apparatus for monitoring a condition of a patient under anaesthesia or sedation, the apparatus comprising:
   detection means for receiving a substantially continuous electrical signal representing a cardiovascular activity of the patient;
   a voltage and/or current dependent circuit detecting each predetermined waveform in said signal;
   first calculation means providing at least one of the following:
      a series of time intervals between successive waveforms, or a series of pressures from successive waveforms, or a series of temporal rates from successive waveforms;
   second calculation means providing successive average values of the series of said time intervals and/or said pressures and/or said temporal rates over a predetermined first time period;

third calculation means providing data about a decrease, or increase respectively in said successive average values; and a display and/or connections into other devices.

30. An apparatus of claim 29, wherein said third calculation means comprises a first calculation unit providing temporally variable derivatives of said successive average values.

31. An apparatus of claim 30, wherein said third calculation means comprises a second calculation unit applying a mathematical operator to said derivatives for providing a selection of accelerations including only those of said temporally variable derivatives which are of a type or types predetermined as relevant and/or fulfil criteria of said type(s) under a second time period.

32. An apparatus of claim 31, wherein said third calculation means comprises a third calculation unit applying a mathematical sliding sum of said selection of accelerations for providing an acceleration index.

33. An apparatus of claim 29, further comprising fourth calculation means connected to said detection means and at least to the second calculation means providing a first predetermined number of heart beats as the first time period into said second calculation means.

34. An apparatus of claim 33, wherein said fourth calculation means is further connected to the second calculation unit of said third calculation means providing a second predetermined number of heart beats as the second time period into said second calculation unit.

35. An apparatus of claim 33, wherein said fourth calculation means is included in a single programmed processor.

36. An apparatus of claim 33, wherein said fourth calculation means is a separate programmed processor.

37. An apparatus of claim 29, wherein said first calculation means, said second calculation means and said third calculation means are a single programmed processor or a combination of several programmed processors.

38. An apparatus of claim 29, wherein at least one of said calculation means: the first calculation means, or the second calculation means, or the third calculation means is a separate programmed processor.

39. An apparatus of claim 29, further comprising memory means for storing at least the values.

40. An apparatus of claim 29, further comprising memory means for storing at least the time periods or numbers therefor.

41. An apparatus of claim 31, further comprising memory means for storing at least the mathematical operators.

42. An apparatus of claim 29, further comprising memory means for storing at least the results of calculations.

* * * * *